(12) United States Patent
Campbell et al.

(10) Patent No.: US 8,309,143 B2
(45) Date of Patent: Nov. 13, 2012

(54) HAIR AND SCALP CARE FORMULATIONS FOR TREATING AND PREVENTING ACNE AND RELATED SKIN CONDITIONS

(76) Inventors: Doreen Campbell, Trabuco Canyon, CA (US); Catherine Parker, Santa Ana, CA (US)

( * ) Notice: Subject to any disclaimer, the term of this patent is extended or adjusted under 35 U.S.C. 154(b) by 0 days.

(21) Appl. No.: 12/762,094

(22) Filed: Apr. 16, 2010

(65) Prior Publication Data

US 2011/0256249 A1 Oct. 20, 2011

(51) Int. Cl.
*A61K 36/752* (2006.01)

(52) U.S. Cl. .................................................. 424/735

(58) Field of Classification Search ................... None
See application file for complete search history.

(56) References Cited

U.S. PATENT DOCUMENTS

| | | | |
|---|---|---|---|
| 5,766,613 | A | 6/1998 | Arraudeau et al. |
| 5,821,237 | A | 10/1998 | Bissett et al. |
| 6,248,343 | B1 | 6/2001 | Jampani et al. |
| 6,294,186 | B1 | 9/2001 | Beerse et al. |
| 6,338,855 | B1 | 1/2002 | Albacarys et al. |
| 6,582,710 | B2 | 6/2003 | Deckers et al. |
| 6,599,513 | B2 | 7/2003 | Deckers et al. |
| 7,150,876 | B2 | 12/2006 | Chaudhuri et al. |
| 7,303,744 | B2 | 12/2007 | Wells et al. |
| 2003/0228272 | A1 | 12/2003 | Amjad et al. |
| 2004/0202684 | A1 | 10/2004 | Djerassi |
| 2005/0136085 | A1 | 6/2005 | Bellamy |
| 2005/0220744 | A1 | 10/2005 | Kamachi et al. |
| 2005/0255060 | A1 | 11/2005 | Oblong et al. |
| 2006/0045896 | A1 | 3/2006 | Morariu |
| 2006/0057075 | A1 | 3/2006 | Arkin et al. |
| 2006/0134246 | A1 | 6/2006 | Wang et al. |
| 2006/0165636 | A1 | 7/2006 | Hasebe et al. |
| 2006/0216251 | A1 | 9/2006 | Morariu |
| 2006/0257509 | A1 | 11/2006 | Zimmerman et al. |
| 2007/0086972 | A1 | 4/2007 | Birnbaum |
| 2007/0254021 | A1 | 11/2007 | Scimeca et al. |
| 2008/0064765 | A1 | 3/2008 | Birnbaum |

FOREIGN PATENT DOCUMENTS

| | | | |
|---|---|---|---|
| CN | 1240640 | A * | 1/2000 |
| DE | 4318280 | A1 * | 12/1993 |
| FR | 2915094 | A1 * | 10/2008 |
| SU | 952257 | B * | 8/1982 |
| WO | WO 03002132 | A1 * | 1/2003 |
| WO | 2004080433 | A1 | 3/2004 |
| WO | 2005034903 | A1 | 4/2005 |
| WO | 2005094777 | A1 | 10/2005 |
| WO | 2005095462 | A1 | 10/2005 |
| WO | 2006075311 | A1 | 7/2006 |
| WO | 2006105450 | A2 | 10/2006 |
| WO | 2006120646 | A1 | 11/2006 |
| WO | 2008015639 | | 2/2008 |

OTHER PUBLICATIONS

"TeensHealth: What Causes Acne". Internet Archive Date: Dec. 4, 2004. [Retrieved from the Internet on: Oct. 28, 2011]. Retrieved from the Internet: <URL: http://web.archive.org/web/20041204232640/http://kidshealth.org/teen/your_body/beautiful/prevent_acne.html>.*

Mayo Clinic Staff. "Skin cancer". Web Publication Date: Aug. 18, 2010. [Retrieved from the Internet on: Oct. 28, 2011]. Retrieved from the Internet: <URL: http://www.mayoclinic.com/health/skin-cancer/DS00190/METHOD=print&DSECTION=all.*

"Treasured Locks: Black Opal Maximum Strength Acne System". Internet Archive Date: May 16, 2008 [Retrieved from the Internet on: Oct. 27, 2011]. Retrieved from the Internet: <URL: http://web.archive.org/web/20080516191458/http://www.treasuredlocks.com/black-opal-maximum-strength-acne-system.html#itemTabs>.*

"Clarifying Complexion-Clearing Shampoo". Internet Archive Date: Apr. 30, 2009 [Retrieved from the Internet on: Oct. 27, 2011]. Retrieved from the Internet: <URL: http://web.archive.org/web/20090430080041/http://www.kairosclearcom/hair-care/clarifying-complexion-clearing-shampoo>.*

(U1) "Cuivridone". Internet Archive Date: Nov. 22, 2008 [Retrieved from the Internet on: Oct. 27, 2011]. Retrieved from the Internet: <URL: http://web.archive.org/web/20081122201435/http://www.solabia.fr/solabia/content/NT00005516.pdf>.*

(V1) "StayC 50/DCM: vitamin A palmitate". Web Publication Date: Jan. 15, 2006 [Retrieved from the Internet on: Oct. 27, 2011]. Retrieved from: <URL: http://www.dsm.com/en_US/downloads/dnpsa/DSM_Product_List.pdf>.*

(W1) "Micro-Derm: Danfree Shampoo for Oily scalp" . Internet Archive Date: Jan. 3, 2008 [Retrieved from the Internet on: Oct. 27, 2011]. Retrieved from the Internet: <URL: http://web.archive.org/web/20080103154913/http://www.microdermlabs.com/anti_dandruff.htm>.*

(X1) "Dermax therapeutic shampoo". Internet Updated date: Feb. 7, 2007 [Retrieved from the Internet on: Oct. 27, 2011]. Retrieved from the Interent: <URL: http://www.netdoctor.co.uk/medicines/100002464.html>.*

(U2) "healthy-skincare.com: Benefit of zinc for Healthy Skin". Internet Archive Date: Oct. 10, 2006 [Retrieved from the Internet on: Oct. 28, 2011]. Retrieved from the Internet: <URL: http://web.archive.org/web/20061010181614/http://www.healthy-skincare.com/benefit-of-zinc.html>.*

(V2) "Segals Solutions: Psoriasis treatment". Internet Archive Date: Aug. 28, 2008 [Retrieved on: Apr. 6, 2012]. Retrieved from the Internet: <URL: http://web.archive.org/web/20080828171351/http://www.segalshairlosstreatment.com/psoriasis-hair-treatment.aspx>.*

(W2) Dial, N. N. Copyright 2007 [Retrieved from the Internet on: Apr. 6, 2012]. Retrieved from the Internet: <URL: http://www.positivearticles.com/Article/How-to-Get-Body-Acne-Under-Control-in-Two-Weeks/15097>.*

(X2) "Scalp Acne". Posting Date: Nov. 6, 2007, Internet Archive Date: Feb. 8, 2008 [Retrieved from the Internet on: Apr. 6, 2012]. Retrieved from the Internet: <URL: http://web.archive.org/web/20080208155652/http://acne.ygoy.com/scalp-acne/>.*

* cited by examiner

*Primary Examiner* — Amy L Clark

(74) *Attorney, Agent, or Firm* — Stetina Brunda Garred & Brucker

(57) ABSTRACT

The present invention is directed to skin treatment formulations having salicylic acid and other secondary ingredients. The secondary ingredients may include: non-comedogenic essential oils and plant extracts and sebum reducing agents. Salicylic acid and the secondary ingredients are provided in amounts effective to provide a sufficiently aggressive skin treatment for unclogging pores and reducing inflammation, while maintaining levels of sebum on the exterior of the skin to form an operative water barrier on the skin and hair. Additionally, a method is provided that unclogs pores, reduces inflammation, and controls levels of sebum on the exterior of the skin to maintain an operative water barrier on the skin and hair. The method may include, applying a sufficiently aggressive product comprising salicylic acid, non-comedogenic plant extracts and essential oils, and a sebum reducing agent to hair and its surrounding areas.

7 Claims, No Drawings

HAIR AND SCALP CARE FORMULATIONS FOR TREATING AND PREVENTING ACNE AND RELATED SKIN CONDITIONS

CROSS-REFERENCE TO RELATED APPLICATIONS

Not Applicable

STATEMENT RE: FEDERALLY SPONSORED RESEARCH/DEVELOPMENT

Not Applicable

BACKGROUND

This invention relates generally to the field of hair and scalp treatment compositions. Specifically, it is directed to non-comedogenic shampoo, conditioner, and scalp formulations for treating skin conditions characterized by clogged pores and oily skin. However, unlike skin treatments of the past, the current invention also serves the dual-purpose of providing a salon quality hair product that cleanses and moisturizes hair. Furthermore, while the shampoo, conditioner, and scalp formulations of the invention are generally applied to the hair and scalp, their therapeutic effects also reach surrounding areas such as the face, neck, chest, shoulders, upper arms and back.

Described as a disease of the pilosebaceous unit, almost all individuals have been affected by acne at one time or another. The pilosebaceous unit is made up of the hair follicle, sebaceous gland, arrector pili muscle, and hair. Although these units are ubiquitous, the largest and most numerous are found on the face, neck, chest, shoulders, upper arms and back, and chest areas, which accounts for the fact that most acne occurs in these regions. The sebaceous gland is responsible for producing sebum, an oily secretion made up of lipids and the debris of fat-producing cells.

Acne is generally associated with several factors, including increase in sebaceous secretions, obstruction of the pilosebaceous unit, abnormal presence of bacteria, and inflammation. The disease is believed to result from a change in the inner lining of the follicle that prevents the sebum from passing through. Although a natural part of the human body, too much or too little production of the substance is undesirable. Under normal conditions, sebum combines with cells that are continually being sloughed from the hair follicle. Once the hair follicle becomes filled with the substance, the sebum spreads to the surrounding skin areas of the face, neck, chest, shoulders, upper arms and back producing an oily appearance. This action is responsible for moisturizing the skin and maintaining its health.

In the diseased state, cells from the inner lining of the follicle shed too fast and clump together. The clumped cells plug the follicle openings preventing the sebum from reaching the surface of the skin. Natural bacteria, which use the sebum as a source of nutrients, grow in the plugged follicles and produce chemicals and enzymes that result in inflammation. Excessive amounts of sebum production can result in the substance being trapped within the hair follicle, resulting in follicular obstruction. The sebum follicle becomes plugged up as sebum produced therein becomes trapped in the follicle. The process of obstructing follicles is known as comedogenesis, with the enlarged follicle plugged with oil and bacteria known as a comedone.

Many products are currently on the market for the treatment of acne. Most require prolonged use and generically work by preventing excessive shedding of cells into the pores, neutralizing excessive bacteria, promoting anti-inflammatory effects, or manipulating hormone levels. Treatment options include contact with benzoyl peroxide or salicylic acid, treatment with antibiotics, topical retinoids, oral retinoids, hormone therapy and use of light based therapies.

Although acne is most commonly associated with the face, neck, chest, shoulders, upper arms and back, hirsute areas such as the scalp are also prone to developing acne. Specifically, unhealthy levels of sebum on the scalp can lead to infection and inflammation of what would otherwise be healthy follicles. The problem becomes compounded because the excess sebum that is excreted onto the scalp transfers onto hair and/or can migrate to surrounding areas of the face, neck, chest, shoulders, upper arms and back, consequently exacerbating acne in those areas. Individuals seeking to eliminate oil on the scalp and hair have turned to harsh shampoos and conditioners. These products have generally consisted of chemicals that "cleanse" by broadly eliminating all of the oil on the hair. As a result, the body produces a greater amount of sebum to compensate for the widespread loss, making matters worse. Furthermore, these products have traditionally consisted of comedogenic chemicals that have produced allergic reactions on the scalp, face, shoulders, and back.

Benzoyl peroxide, although an effective anti-acne agent that fights bacteria and removes dead skin, cannot be incorporated in a dual-purpose hair product because of its harsh effects on hair. In fact, benzoyl peroxide is such a harsh product that it will change the color of any hair that it comes into contact with. Treatments using other medications are either not effective, require permission from a physician, are cost prohibitive, and/or have unwanted side effects. Topical formulations containing antibacterial agents which prevent excess dirt or bacteria buildup on the hair follicles are not always effective and may result in drying of the scalp. As previously described, shampoos have been designed with compounds that remove excess oil. However, in developing topical formulations to treat oily hair, effectiveness often becomes a balancing act. Too much oil production causes acne; too harsh of an oil removing formulation results in dry, irritated skin, and hair that is harsh, rough, subject to static electricity, dull, and hard to detangle. Therefore in a dual-purpose product, it is important to maintain a healthy balance of sebum on the skin and hair. The proper balance is struck where enough sebum is left to lubricate and maintain a protective water barrier on the skin and hair, yet not enough to noticeably exacerbate acne.

Salicylic acid is one tool that has been widely used in the treatment of conditions characterized by excess production of skin cells and inflammation. It is largely held that it is the antimicrobial, anti-inflammatory and keratolytic effects of salicylic acid that aid in the treatment of such conditions. Salicylic acid has been used to treat these conditions in a variety of forms, one of which is shampoo. However, incorporating salicylic acid into shampoo is difficult because it has poor solubility in water. Incorporation therefore requires carefully weighed ratios of salicylic acid to suspension agent. In addition to this difficulty, the use of active ingredients in shampoos has further problems. To that point, application Ser. No. 11/194,582 to Arkin et al. describes disadvantages such as the danger of contact between an active ingredient in the shampoo and the eyes of a treated individual.

It has also been found that secondary ingredients can play a large role alongside salicylic acid in the treatment of some skin conditions. For example, application Ser. No. 10/397,155 to Amjad, et al. teaches the addition of tea tree leaf oil to dandruff treating shampoos. However, as Amjad et al. also discloses, oils have their own difficulties in combination with shampoos because they are incompatible with the surfactants therein. This incompatibility makes for an unsatisfactory product as to foam, lather, and cleansing properties.

While the incorporation of salicylic acid and other secondary ingredients in shampoos has the above-mentioned problems, these difficulties are only compounded in the case of acne treatment. Due to the hypersensitivity of an afflicted person's skin, the slightest shift in conditions, e.g. increased or decreased sebum, bacteria, exfoliation, etc., can result in exacerbation of the condition. Proper treatment therefore requires a product that incorporates primary and secondary ingredients in just the right amounts. Although many ingredients have desirable properties for use in acne treatment, unfortunately, if not added in the correct quantity or ratio as to the other ingredients, their use will result in unwanted effects. This balance is especially important in a product designed to treat acne and cleanse and condition hair.

Therefore, what is needed is a dual-purpose, non-comedogenic, non-sebum producing formula that can be used as a shampoo, conditioner, and/or scalp treatment which cleans and moisturizes hair while treating acne and related skin conditions on the scalp and surrounding areas by unclogging pores and only maintaining an amount of sebum sufficient to lubricate and protect the skin and hair.

BRIEF SUMMARY

The present invention is directed to a non-comedogenic hair and scalp treatment formulation comprising salicylic acid and a plurality of secondary ingredients, the plurality of secondary ingredients comprise at least one non-comedogenic essential oil, at least one non-comedogenic plant extract, and at least one sebum reducing agent, wherein salicylic acid and the plurality of secondary ingredients are provided in amounts effective to provide a sufficiently aggressive skin treatment for unclogging pores and significantly reducing prostaglandin production in afflicted skin cells to reduce inflammation, while maintaining levels of sebum on the exterior of the skin to form an operative water barrier on the skin and hair. The formulations are effective when used as an acne prevention treatment, and are unique in providing a cleansing and moisturizing agent for the hair, while concomitantly preventing or significantly reducing the incidence of acne in surrounding skin areas such as the face, neck, chest, shoulders, upper arms and back which historically were adversely affected by prior art hair and scalp treatments containing comedogenic secondary ingredients.

In one embodiment of the invention the at least one essential oil has antibacterial, antifungal, and antiviral properties.

In another embodiment of the current invention, along with having antibacterial, antifungal, and antiviral properties the at least one essential oil also may have anti-inflammatory properties.

In a further embodiment of the invention the at least one plant extract has antibacterial and antioxidant properties.

In yet another embodiment of the current invention the at least one essential oil has antioxidant and astringent properties.

In another embodiment of the invention the at least one sebum reducing agent is a metallic salt that has astringent properties.

In yet another embodiment of the invention the at least one sebum reducing agent is a carboxylic acid having exfoliating properties.

In one embodiment of the invention the operative water barrier is sufficient to reduce static electricity in the hair.

The at least one non-comedogenic essential oil may comprise sweet almond oil, tea tree oil, and lavender oil, and the at least one non-comedogenic plant extract may comprise *Iris Florentina* root extract, *Sapindus Mukurossi* fruit extract, and *Anthemis Nobilis* flower extract, and the at least one sebum reducing agent may comprise copper PCA.

In another embodiment of the invention, salicylic acid is provided at about 0.5% to 2.0% w/w, and the plurality of secondary ingredients may be provided in the following ranges: sweet almond oil at about 0.5% to 30% w/w, tea tree oil, lavender oil, *Sapindus Mukurossi* fruit extract, *Anthemis Nobilis* flower extract, and copper PCA all at about 0.1% to 1.0% w/w, and *Iris Florentina* root extract at about 0.1% to 10% w/w.

In a further embodiment of the invention salicylic acid is provided at about 1.0% w/w.

In one embodiment of the invention the non-comedogenic hair and scalp treatment further comprises retinyl palmitate at about 0.1% to 1.0% w/w, and zinc sulfate at about 0.1% to 10% w/w.

In another embodiment of the invention, the at least one sebum reducing agent may comprise lactic acid and copper PCA, the at least one noncomedogenic essential oil may comprise tea tree oil, and lavender oil, and the at least one noncomedogenic plant extract may comprise *Anthemis Nobilis* flower extract, and *Sapindus Mukurossi* fruit extract.

Salicylic acid may be provided at about 0.5% to 2.0% w/w, and the plurality of secondary ingredients may be provided in the following ranges: tea tree oil, lavender oil, *Anthemis Nobilis* flower extract, *Sapindus Mukurossi* fruit extract, copper PCA, and lactic acid all at about 0.1% to 10% w/w.

In another embodiment of the invention the non-comedogenic hair and scalp treatment formulation may further comprise retinyl palmitate, and the at least one noncomedogenic essential oil may further comprise sweet almond oil. The at least one noncomedogenic plant extract may further comprise *Iris Florentina* root extract, and the at least one sebum reducing agent may further comprise benzalkonium chloride.

In the next embodiment of the invention salicylic acid may be provided at about 0.5% to 2.0% w/w, the plurality of secondary ingredients may be provided in the following ranges: tea tree oil, lavender oil, *Anthemis Nobilis* flower extract, *Sapindus Mukurossi* fruit extract, copper PCA, and lactic acid all at about 0.1% to 10% w/w, *Iris Florentina* root extract may be provided at about 0.1% to 10% w/w, and benzalkonium chloride may be provided at about 0.1% to 1.0% w/w.

In one embodiment of the invention the at least one non-comedogenic essential oil may comprise tea tree oil, lavender oil, and sweet almond oil, and the at least one noncomedogenic plant extract may comprise *Anthemis Nobilis* flower extract, and *Sapindus Mukurossi* fruit extract, and the at least one sebum reducing agent may comprise lactic acid and copper PCA.

In another embodiment of the invention salicylic acid may be provided at about 0.5% to 2.0% w/w, and the plurality of secondary ingredients may be provided in the following ranges: tea tree oil, lavender oil, and sweet almond oil all at about 0.1% to 10% w/w, *Anthemis Nobilis* flower extract and *Sapindus Mukurossi* fruit extract each at about 0.1% to 10% w/w, and lactic acid and copper PCA both at about 0.1% to 10% w/w.

In a further embodiment of the invention the at least one noncomedogenic plant extract may further comprise *Iris Flo-*

*rentina* root extract, and the at least one sebum reducing agent may further comprise benzalkonium chloride.

In another embodiment, salicylic acid may be provided at about 0.5% to 2.0% w/w, tea tree oil, lavender oil, and sweet almond oil may all be provided at about 0.1% to 10% w/w, *Anthemis Nobilis* flower extract and *Sapindus Mukurossi* fruit extract each may be provided at about 0.1% to 10% w/w, lactic acid and copper PCA both may be provided at about 0.1 to 10% w/w, benzalkonium chloride may be provided at about 0.1% to 1.0% w/w, and *Iris Florentina* root extract may be provided at about 0.1% to 10% w/w.

In another embodiment, the present invention is directed to a method of treating skin conditions by unclogging pores, significantly reducing prostaglandin production in afflicted skin cells to reduce inflammation, and controlling levels of sebum on the exterior of the skin to maintain an operative water barrier on the skin and hair. Specifically, the method comprises applying a product comprising salicylic acid, a non-comedogenic essential oil, a non-comedogenic plant extract, and a sebum reducing agent, to hair and the hair's surrounding areas.

Accordingly, it is a primary objective of the instant invention to provide a multi-substance formulation for use on the hair and scalp or surrounding areas for treating skin conditions related to clogged pores, over or under production of sebum, inflammation, and/or excessive production of skin cells.

It is a further objective of the instant invention to provide a multi-substance treatment shampoo for use on conditions related to clogged pores, over or under production of sebum, inflammation and/or excessive production of skin cells.

It is yet another objective of the instant invention to provide a multi-substance treatment conditioner for use on conditions related to clogged pores, over or under production of sebum, inflammation and/or excessive production of skin cells.

It is a still further objective of the invention to provide a multi-sub stance scalp treatment formulation for use on conditions related to clogged pores, over or under production of sebum, inflammation and/or excessive production of skin cells.

Other objects and advantages of this invention will become apparent from the following description.

DETAILED DESCRIPTION

The present invention describes a hair and scalp treatment comprised of a variety of non-comedogenic compounds that synergistically treat acne and other related skin conditions. The ingredients of the formulations are provided at specific ratios to treat afflicted skin, prevent acne and other inflammatory skin conditions, as well as moisturize, condition, and cleanse hair.

Embodiments of the invention include a shampoo, conditioner, and/or scalp treatment. The formulations are effective when used to treat and prevent conditions related to clogged pores, over or under production of sebum, inflammation and/or excessive production of skin cells, and are unique in providing a cleansing and moisturizing agent for the hair, while concomitantly preventing or significantly reducing the incidence of such conditions in surrounding skin areas, such as the face, neck, chest, shoulders, upper arms and back, which, historically, were adversely effected by prior art hair and scalp treatments containing comedogenic secondary ingredients.

Accordingly, the shampoo, conditioner, and scalp treatments are comprised of ingredients having non-comedogenic effects individually or in combination. These ingredients are therapeutically advantageous for a variety of reasons. For example, many of the ingredients have been chosen because they have antimicrobial, anti-inflammatory, antifungal, antiseptic, stabilizing, preservative, astringent, sebum reducing, antioxidant, and/or exfoliating properties. At a more basic level, the formulations of the current invention include: (1) salicylic acid, (2) solvents, (3) conditioners, (4) non-comedogenic essential oils, (5) non-comedogenic plant extracts, (6) sebum reducing agents, (7) stabilizing agents, and (8) preservatives. Fragrance can also be added to the formulations.

Common to all embodiments of the invention is the incorporation of various non-comedogenic essential oils and plant extracts. These types of compounds have been scientifically tested for their potential as natural alternatives to synthetic compounds used to treat a variety of ailments. Those tests have shown that these natural compounds possess anti-inflammatory, antibacterial, antifungal, antiviral, insecticidal, and antioxidant properties. Some oils have been used to treat cancer. Others have been used in food preservation, aromatherapy and fragrance industries. They are a group rich in biologically active compounds.

One important characteristic of essential oils and their components is their hydrophobicity, which enables them to partition the lipids of bacterial cell membranes and mitochondria, disturbing the cell structures and rendering them more permeable. This same property allows them to penetrate the inside of pores and target harmful microbials where they have built up amongst the sebum. Once contacted, the compounds will interact with the bacteria, causing extensive leakage from bacterial cells and the exit of critical molecules and ions. This leakage results in widespread elimination of the bacteria.

The non-comedogenic plant extracts and essential oils having antioxidant properties work synergistically with the other ingredients of the current invention to treat a variety of skin conditions. Oxidation is a biological reaction that occurs at an intercellular atomic level. It occurs when a reducing substance interacts with an oxidizing substance and donates electrons to it. These interactions can produce free radicals that start chain reactions that can damage DNA, proteins, and lipids. The non-comedogenic ingredients having antioxidant properties act to receive free radicals, stopping harmful chain reactions and inhibiting new chain reactions by acting as oxidizers themselves.

A more detailed description of the ingredients used in different embodiments of the current invention is provided below.

Salicylic Acid

Salicylic acid is used in the preferred embodiment of the current invention. Salicylic acid, a beta hydroxy acid (BHA), serves multiple purposes in the treatment of skin conditions. First, it acts as a keratolytic, stripping the dead skin cells from the outer surface of the treated area and surrounding skin areas. The exfoliation of the dead cells provides a therapeutic effect because it prevents pores from clogging and allows new, healthy cells, to take their place. In addition to sloughing dead skin from the treated area, salicylic acid is also useful in treating skin conditions because it reduces bacteria in the afflicted areas. Importantly, it is soluble in oil and can therefore penetrate the pores to eliminate bacteria where they have taken root around the built up sebum.

In the current invention, salicylic acid plays another particularly important role. Acne and related skin conditions are almost always accompanied by widespread inflammation and pain in and around the surrounding areas of the skin. These unfortunate symptoms are in large part due to high levels of prostaglandins in the damaged cells. Salicylic acid counteracts the production of these lipid compounds by inhibiting enzymes involved in their biosynthesis, particularly COX-1 and COX-2. Therefore, after first stripping the affected areas of dead skin cells, and ridding the pores of bacteria, salicylic acid can then significantly reduce pain and swelling while the skin heals and returns to a healthy state.

Ingredients from the following list may be used in combination with salicylic acid and/or the other secondary ingredients and are considered to be within the scope of the current invention: benzoic acid, 2-hydroxybenzoic acid, o-carboxyphenol, phenol-2-carboxylic acid, benzoic acid, retinoic acid, tretinoin, tazarotene, isotretinoin, benzoyl peroxide, clindamycin, sulfur, sulfur with sodium sulfacidamide, erythromycin, corticosteroid, adapalene, azelaic acid, dapsone gel, nadifloxacin, aknemycin, glycolic acid, resorcinol, micanozole nitrate, tacrolimus, chloroxylenol, triclosan, alpha hydroxy acid, gluconolactone, metronizadol, and hexachlorophene. These are generally only available by prescription.

Formulations of the present invention may also include non-prescription based acne medical treatments, including but not limited to, retinols, benzoyl peroxide 2.5%-5%, sulfur 3-10%, resorcinol 2%, alpha hydroxy acid, glycolic acid, and hexetidin.

Sodium Coco-Sulfate

Sodium Coco Sulfate is a naturally derived alternative to Sodium Lauryl Sulfate in flake form, often used as a surfactant. Sodium Coco Sulfate is derived from pure coconut oil. It can be used in various personal care applications in which viscosity building and foam characteristics are of importance. The product formulates similar to synthetic alkyl sulfates, but is less defatting to the hair and skin. Because Sodium Coco Sulfate is less soluble than synthetic alkyl sulfates, it leaves the skin and hair with a conditioned feel. Commercial use includes incorporation into shampoos, hand soaps, bath products, shaving creams and medicated ointments.

Equivalents considered to be within the scope of the current invention are: sulfuric acid, monococoyl ester, sodium salt, sulfuric acid, monococoyl ester, and monococo alkyl esters.

Cocamidopropyl Betaine

Cocamidopropyl betaine (CAPB) is a zwitterionic surfactant with a quaternary ammonium cation in its molecule. It is a derivate of cocamide and glycine betaine. It is used as a surfactant or foaming agent in bath products like shampoos and hand soaps. Cocamidopropyl betaine is milder on the skin than the benzine sulfonates, reducing the amount of harsher detergents that need to be added. It also has certain antibiotic properties that can prevent spoiling of the shampoo. In cosmetics, it is used as an emulsifying agent and thickener. It may also be used to reduce irritation caused by surfactants. In hair conditioners, it can serve as an antistatic agent.

Equivalents considered to be within the scope of the current invention are: CADG, N-(carboxymethyl)-N,N-Dimethyl-3-[(1-oxococonut)amino]-1-propanaminium hydroxide, cocamido betaine, cocamidopropyl dimethyl glycine, cocoyl amide propylbetaine, cocoyl amide propyldimethyl glycine, cocoyl amide propyldi methyl glycine solution, 1-propanaminium, hydroxide, and quaternary ammonium compounds.

Cocamide MEA

Cocamide MEA, or cocamide monoethanolamine, is a pale yellow viscous clear to amber liquid or solid flakes. It can be made from fatty acids in coconut oils, reacted with ethanolamine. Cocamide ethanolamines are used as foaming agents and cationic surfactants in shampoos and bath products, and as emulsifying agents in cosmetics.

Equivalents considered to be within the scope of the current invention are: N-(2-hydroxyethyl), coco monoethanolamide, coconut fatty acid monoethanolamide, cocoyl monoethanolamine, equex AEM, and coco fatty acid amide.

Zinc Sulfate

Zinc sulfate is a colorless crystalline, water-soluble chemical compound that has astringent properties.

Polysorbate 80

Polysorbate 80 (commercially also known as TWEEN 80, a registered trademark of ICI Americas, Inc.) is a nonionic surfactant and emulsifier derived from polyoxylated sorbitan and oleic acid, and is often used in foods. Polysorbate 80 is a viscous, water-soluble yellow liquid. The hydrophilic groups in this compound are polyethers also known as polyoxyethylene groups which are polymers of ethylene oxide. The numeral designation following polysorbate refers to the lipophilic group, which for polysorbate-80 is the oleic acid.

Polysorbate 20

Polysorbate 20, commercially known as TWEEN 20) is a polysorbate surfactant whose stability and relative non-toxicity allows it to be used as a detergent and emulsifier in a number of domestic, scientific and pharmacological applications. It is a polyoxyethylene derivative of sorbitan monolaurate, and is distinguished from the other members in the Tween range by the length of the polyoxyethylene chain and the fatty acid ester moiety. The commercial product contains a range of chemical species.

Sodium Cocoyl Apple Amino Acids

Sodium Cocoyl Apple Amino Acid is a fruit surfactant, derived from apple juice essential amino-acids and can be used as a sulfate-free cleansing agent. In addition, it can be used as an anti-aging and conditioning agent.

Lactic Acid

Lactic acid acts to reduce sebum in a way similar to salicylic acid. It strips the treated area of dead skin cells, unclogging pores. It then penetrates the pores and removes bacteria that are situated therein. The sebum levels in the treated pores can then return to a regular level.

Equivalents considered to be within the scope of the current invention are: A-hydroxypropanoic acid, and propanoic acid.

Copper PCA

Copper PCA is the copper salt of L-Pyrrolidone Carboxylic Acid or L-PCA, a physiological component of the epidermis, obtained by cyclisation of glutamic acid. It is used to reduce sebum production by performing an astringent function.

An equivalent considered to be within the cope of the current invention is BIS (5-oxo-L-prolinato-N1, 02) Copper.

*Melaleuca Alternifolia* (Tea Tree) Leaf Oil

*Melaleuca Alternifolia* (Tea Tree) Leaf Oil is a volatile essential oil derived mainly from the Australian native plant *Melaleuca alternifolia*. This oil easily and quickly penetrates the skin, serving as an antibacterial and disinfecting agent and is known to accelerate the healing of skin irritations and infections. *Melaleuca Alternifolia* (Tea Tree) Leaf Oil is incorporated as the active ingredient in many topical formulations used to treat cutaneous infections. It is composed of terpene hydrocarbons, mainly monoterpenes, sesquiterpenes, and their associated alcohols. Terpenes are volatile, aromatic hydrocarbons and may be considered polymers of isoprene, which has the formula $C_5H_8$. It is known to have antibacterial, antifungal, antiviral, and anti-inflammatory properties.

*Lavandula Angustifolia* (Lavender) Oil/Flower Extract

Lavender oil is an essential oil obtained by distillation from the flower spikes of certain species of lavender. Two forms are distinguished, Lavender Flower Oil, a colorless oil, insoluble in water, having a density of 0.885 (g/mL); and Lavender Spike Oil, a distillate from the herb *Lavandula latifolia*, having density 0.905. Lavender Flower Oil is a designation of the National Formulary and the British Pharmacopoeia. It is not a pure compound; it is a complex mixture of natural products. The primary components of lavender oil are linalool (51%) and linalyl acetate (35%) [6]. Other components include a-pinene, limonene, 1,8-cineole, cis- and trans-ocimene, 3-octanone, camphor, caryophyllene, terpinen-4-ol and lavendulyl acetate. It is known to have anti-bacterial, anti-fungal, anti-viral, anti-inflammatory, and antiseptic properties.

*Prunus Amygdalus Dulcis* (Sweet Almond) Oil

*Prunus Amygdalus Dulicis* oil is derived from the kernel of the sweet almond and works well as an emollient because of its relatively low (17%) essential fatty acid content as compared to other essential oils. It is also high in vitamin E and acts as a moisturizer. Because of its high vitamin E content, sweet almond oil has antioxidant properties. Sweet almond oil is also used as an antibacterial agent.

*Acai* extract is known in the art as an antioxidant and is an equivalent of sweet almond oil.

*Anthemis Nobilis* (German Chamomile) Flower Extract

Chamomile oil is derived from the flowers of the chamomile plant. There are two types of chamomile, Roman and German, both of which are used for their essential oils. While the medicinal properties of the two are very similar, for example, they both have antibacterial properties, German Chamomile is a stronger anti-inflammatory due to presence of a compound called Azulene.

*Sapindus Mukurossi* Fruit Extract

*Sapindus Mukurossi* fruit is known as soap nut, soapberry, washnut, tiha, reetha, aritha, dodan, and doadni. It is a deciduous tree widely grown in upper reaches of Indo Gangetic plains, Shivaliks and sub Himalayan tracts at altitudes from 200 m to 1500 m. It provides a less irritating alternative to modern chemical formulations used for a variety of purposes. *Sapindus Mukurossi* fruit extract has cleansing, anti-bacterial, and anti-fungal, among other properties. These properties have been attributed to the saponin found therein. Saponins have a diverse range of properties, including foaming and emulsifying, pharmacological and medicinal, and haemolytic properties, as well as antimicrobial, insecticidal, spermicidal and molluscicidal activities.

*Iris Florentina* Root Extract

*Iris Florentina* is an iris species native to Italy. The iris's rhizomatous root, can be steam distilled to create a cream-colored, waxy substance called orris butter. The essential oil derived from this root has been used to treat dropsy, or swelling from an accumulation of water. The dried root is considered a diuretic and expectorant.

Retinyl Palmitate

Retinyl palmitate is also known as vitamin A palmitate. It is an ester of retinol (vitamin A) and palmitic acid. It is also the major component of palm oil. It is an antioxidant and when put on the skin, it is converted to retinol, and ultimately to retinoic acid. Retinyl palmitate also reduces the size and secretion of the sebaceous glands and reduces bacterial numbers therein.

Methylheptyl Isostearate

Methylheptyl Isostearate is the ester of caprylic alcohol and isotearic acid. It is a conditioning agent.

Polyquaternium-44

Polyquaternium-44 is a very efficient, multifunctional polymer for use in a variety of cleansing products to improve the wet combing ability of the hair and prevent electrostatic charging when the hair is dry. It also protects the hair by forming a shield around each hair so that its surface is less readily attacked. It conditions and provides a smooth silky feel to the hair.

Methychloroisothiazolinone

Methylchloroisothiazolinone (5-chloro-2-methyl-4-isothiazolinon-3-one) is a preservative with antibacterial and antifungal effects within the group of isothiazolinones. It is effective against gram-positive and gram-negative bacteria, yeast and fungi. It is found in many water-based personal care products and cosmetics and is used in glue production, detergents, paints, fuels and other industrial processes.

Equivalents considered to be within the scope of the current invention are: 5-chloro-2-methyl-4-isothiazoline-3-one, 4-isothiazoline-3-one, methylchlorothiazolinone, and 3(2H) isothiazolone.

Methylisothiazolinone

Methylisothiazolinone is a powerful biocide and preservative within the group of isothiazolinones used in shampoos and body care products.

Equivalents considered to be within the scope of the current invention are: 2-methyl-3(2H)-isothiazolone; and 2-methyl-4-isothiazolin-3-one.

Benzalkonium Chloride

Benzalkonium Chloride has an antibacterial property thought to be due to its ability to disrupt intermolecular interactions. By penetrating cellular membranes, it induces leakage of bacteria intercellular contents. Therefore, solutions containing Benzalkonium Chloride are active against bacteria, some viruses, fungi, and protozoa. The exact percentages of other ingredients in a Benzalkonium Chloride solution must be moderated carefully because these types of solutions can readily be inactivated by the presence of certain other secondary ingredients.

Stearyl Alcohol

Stearyl alcohol (also known as octadecyl alcohol or 1-octadecanol) is a substance prepared from stearic acid by the process of catalytic hydrogenation. It is a fatty alcohol, which takes the form of white solid granules or flakes which are insoluble in water, with a melting point of 61° C. and boiling point of 210° C. (at 15 mmHg). It has a wide range of uses as an ingredient in lubricants, resins, perfumes and cosmetics. It is used as an emollient, emulsifier, and thickener in ointments of various sorts, and is widely used as a hair coating in shampoos and hair conditioners. Octadecyl alcohol is even used as a liquid solar blanket in swimming pools by forming a molecule thick layer on the surface of the water and slowing the evaporation rate of the pool water. Its chemical formula is $CH_3(CH_2)_{17}OH$.

Butylene Glycol

Butylene glycol is a common humectant and solvent used in cosmetic and food preparations.

Propylene Glycol

Propylene glycol is a fairly viscous liquid at room temperature and has been used for a number of its properties. It is used as a solvent and emulsification agent because of its solubility in water and oil, as well as its ability to thicken a solution.

Cetyl Alcohol

Cetyl alcohol, also known as 1-hexadecanol and palmityl alcohol, is a solid organic compound and a member of the alcohol class of compounds having a chemical formula of $CH_3(CH_2)_{15}OH$. It belongs to the group of fatty alcohols. At room temperature, cetyl alcohol takes the form of a waxy white solid or flakes. Cetyl alcohol is used in the cosmetic industry as a surfactant in shampoos, or as an emollient, emulsifier or thickening agent in the manufacture of skin creams and lotions.

Brassicamidopropyl Dimethylamine

Brassicamidopropyl Dimethylamine is a conditioning ingredient derived from Brassicacae oil.

Potassium Sorbate

Potassium sorbate is a potassium salt that is widely used as a food and personal care preservative. It has antimicrobial and antifungal properties that are useful in maintaining the shelf life of such products.

Panthenol

Panthenol is the alcohol analog of pantothenic acid (vitamin B5), and is thus the provitamin of B5. In organisms it is quickly oxidized to pantothenate. Panthenol is a highly viscous transparent liquid at room temperature, but salts of pantothenic acid (for example sodium pantothenate) are powders (typically white). It is well soluble in water, alcohol and propylene glycol, soluble in ether and chloroform, and slightly soluble in glycerin. Panthenol comes in two enantiomers, D and L. Only D-panthenol (dexpanthenol) is biologically active, however both forms have moisturizing properties. For cosmetic use, panthenol comes either in D form, or as a racemic mixture of D and L (DL-panthenol). Pantothenol's expanded chemical formula is: HO—CH2-C(CH3)2-CH(OH)—CONH—CH2CH2CH2-OH. Panthenol is a humectant, emollient and moisturizer. It binds to hair follicles readily and is a frequent component of shampoos and hair conditioners (in concentrations of 0.1-1%). It coats the hair and seals its surface, lubricating follicles and making strands appear shiny.

Equivalents considered to be within the scope of the invention are: dexpanthenol, pantothenol, pantothenyl alcohol, D-pantothenyl alcohol, DL-pantothenyl alcohol.

Tetrasodium EDTA

Ethylenediaminetetraacetic acid is a chelating agent for metallic ions, abbreviated EDTA. Tetrasodium EDTA is the most common form in commerce, but other metallic chelates are marketed, for example, iron, zinc, and calcium. Tetrasodium EDTA is a white solid, very soluble in water and forming a basic solution. Prepared from ethylenediamine, formaldehyde, and sodium cyanide in basic solution, or from ethylenediamine and sodium chloroacetate, EDTA is a strong complexing and chelating agent. It reacts with many metallic ions to form soluble chelates. As such, it is widely used in analysis to retain alkaline earths and heavy metals in solution.

Equivalents considered to be within the scope of the invention are: edetate sodium, and N,N'-1,2-ethanediylbis[N-carboxymethyl)glycine].

Xanthan Gum

Xanthan gum is a polysaccharide used as a food additive and rheology modifier. It is produced by a process involving fermentation of glucose or sucrose by the *Xanthomonas campestris* bacterium. The backbone of the polysaccharide chain consists of two β-D-glucose units linked through the 1 and 4 positions. The side chain consists of two mannose units and one glucuronic acid, so the chain consists of repeating modules of five sugar units. The side chain is linked to every other glucose of the backbone at the 3 position. About half of the terminal mannose units have a pyruvic acid group linked as a ketal to its 4 and 6 positions. The other mannose unit has an acetyl group at the 6 positions. Two of these chains may be aligned to form a double helix, giving a rather rigid rod configuration that accounts for its high efficiency as a viscosifier of water. The molecular weight of xanthan varies from about one million to 50 million depending upon how it is prepared. It is commonly added to cosmetic products as a stabilization and binding agent, preventing individual agents from separating.

DMDM Hydantoin

DMDM hydantoin is a preservative that works by releasing formaldehyde into the product.

Compounds which are anti-inflammatory, antibacterial/anti-microbial, anti-oxidant, and astringents which are in accordance with the present invention include, *aloe vera*, barberry, birch, burdock, calendula, chlorophyll, colloidal silver, comfrey, dandelion, fenugreek, flaxseed oil, garlic, ginger, horsetail, hyssop, L-cysteine, lemongrass, marshmallow, myrrh, Oregon grape, plantain, primrose oil, selenium, shark cartilage, slippery elm, vitamin A, vitamin B, vitamin C, vitamin D, vitamin E, white oak, witch hazel, yellow dock, zinc, chamomile, sea fennel, licorice, sulfur, hops, nettle, carrot seed, hawthorn, grape fruit seed, and triclosan.

Compounds which offer protection against sun exposure, such as Chaparral, are useful in accordance with the present invention.

Compounds which sooth skin, such as elder flower are useful in accordance with this invention.

Compounds which moisturize dry hair, such as Irish moss, are useful in accordance with this invention.

Compounds which promote shiny hair, such as sage, are useful in accordance with this invention.

The beneficial composition as instantly disclosed and claimed was developed to provide a formulation for treating conditions related to clogged pores, over or under production of sebum, inflammation and/or excessive production of skin cells. The combination of ingredients provides a unique non-comedogenic, non-sebum producing group of formulations useful as a shampoo, conditioner, or scalp treating agent. Among the many ingredients are substances which are combined to provide a formulation which, when applied to the head, not only prevents clogging of pores on the scalp while cleaning and moisturizing the hair, but also prevents exacerbating the individual's condition upon the surrounding skin of the face, neck, chest, shoulders, upper arms and back while concomitantly reducing irritation of the skin upon use, keeping sebum at a normal level, promoting healthy exfoliation, and reducing harmful bacteria in and around the pores.

EXAMPLE 1

One particular, albeit non-limiting formulation that can be used as a shampoo includes the following substances added in the following approximate amounts:

| SUBSTANCE | WT/WT % Ranges |
| --- | --- |
| Salicylic Acid | 0.5-2.0 |
| Non-Comedogenic Secondary Ingredients (other ingredients) | |
| Water | 30.0-100 |
| Sodium Coco-Sulfate | 0.1-30.0 |
| Cocamidopropyl Betaine | 0.1-30.0 |
| Cocamide MEA | 0.1-30.0 |
| Sodium Cocoyl Apple Amino Acids | 0.1-30.0 |
| Lactic Acid | 0.1-10.0 |
| Copper PCA | 0.1-10.0 |
| Polysorbate 20 | 0.1-30.0 |
| *Malaleuca Alternifolia* (Tea Tree) Leaf Oil | 0.1-10.0 |
| *Lavandula Angustifolia* (Lavender) Oil | 0.1-10.0 |
| *Anthemis Nobilis* Flower Extract | 0.1-10.0 |
| *Sapindus Mukurossi* Fruit Extract | 0.1-10.0 |

EXAMPLE 2

A second formulation that can be used as a shampoo incorporates additional ingredients and includes the following substances added in the following approximate amounts:

| SUBSTANCE | WT/WT % Ranges |
|---|---|
| Salicylic Acid Non-Comedogenic Secondary Ingredients (other ingredients) | 0.5-2.0 |
| Water | 30.0-100 |
| Sodium Coco-Sulfate | 0.1-30.0 |
| Cocamidopropyl Betaine | 0.1-30.0 |
| Cocamide MEA | 0.1-30.0 |
| Sodium Cocoyl Apple Amino Acids | 0.1-30.0 |
| Lactic Acid | 0.1-10.0 |
| Copper PCA | 0.1-10.0 |
| Polysorbate 20 | 0.1-30.0 |
| *Malaleuca Alternifolia* (Tea Tree) Leaf Oil | 0.1-10.0 |
| *Lavandula Angustifolia* (Lavender) Oil | 0.1-10.0 |
| *Anthemis Nobilis* Flower Extract | 0.1-10.0 |
| *Sapindus Mukurossi* Fruit Extract | 0.1-10.0 |
| Alcohol | 0.1-10.0 |
| *Prunus Amygdalus Dulcis* (Sweet Almond) Oil | 0.1-10.0 |
| Propylene Glycol | 0.1-10.0 |
| Iris Florentina Root Extract | 0.1-10.0 |
| Zinc Sulfate | 0.1-10.0 |
| Retinyl Palmitate | 0.1-1.0 |
| Polyquaternium-44 | 0.1-1.0 |
| Methylchloroisothiazolinone | 0.1-1.0 |
| Methylisothiazolinone | 0.1-1.0 |
| Benzalkonium Chloride | 0.1-1.0 |
| Fragrance | 0.1-1.0 |

EXAMPLE 3

The shampoo as illustrated in Example 1 having the ingredient of Salicylic Acid used at 0.5% wt/wt.

| SUBSTANCE | WT/WT % Ranges |
|---|---|
| Salicylic Acid Non-Comedogenic Secondary Ingredients (other ingredients) | 0.5 |
| Water | 30.0-100 |
| Sodium Coco-Sulfate | 0.1-30.0 |
| Cocamidopropyl Betaine | 0.1-30.0 |
| Cocamide MEA | 0.1-30.0 |
| Sodium Cocoyl Apple Amino Acids | 0.1-30.0 |
| Lactic Acid | 0.1-10.0 |
| Copper PCA | 0.1-10.0 |
| Polysorbate 20 | 0.1-30.0 |
| *Malaleuca Alternifolia* (Tea Tree) Leaf Oil | 0.1-10.0 |
| *Lavandula Angustifolia* (Lavender) Oil | 0.1-10.0 |
| *Anthemis Nobilis* Flower Extract | 0.1-10.0 |
| *Sapindus Mukurossi* Fruit Extract | 0.1-10.0 |

EXAMPLE 4

The shampoo as illustrated in Example 2 having the ingredient of Salicylic Acid used at 0.5% wt/wt.

| SUBSTANCE | WT/WT % Ranges |
|---|---|
| Salicylic Acid Non-Comedogenic Secondary Ingredients (other ingredients) | 0.5 |
| Water | 30.0-100 |
| Sodium Coco-Sulfate | 0.1-30.0 |
| Cocamidopropyl Betaine | 0.1-30.0 |
| Cocamide MEA | 0.1-30.0 |
| Sodium Cocoyl Apple Amino Acids | 0.1-30.0 |
| Lactic Acid | 0.1-10.0 |
| Copper PCA | 0.1-10.0 |
| Polysorbate 20 | 0.1-30.0 |
| *Malaleuca Alternifolia* (Tea Tree) Leaf Oil | 0.1-10.0 |
| *Lavandula Angustifolia* (Lavender) Oil | 0.1-10.0 |
| *Anthemis Nobilis* Flower Extract | 0.1-10.0 |
| *Sapindus Mukurossi* Fruit Extract | 0.1-10.0 |
| *Prunus Amygdalus Dulcis* (Sweet Almond) Oil | 0.1-10.0 |
| Alcohol | 0.1-10.0 |
| Propylene Glycol | 0.1-10.0 |
| *Iris Florentina* Root Extract | 0.1-10.0 |
| Zinc Sulfate | 0.1-10.0 |
| Retinyl Palmitate | 0.1-1.0 |
| Polyquaternium-44 | 0.1-1.0 |
| Methylchloroisothiazolinone | 0.1-1.0 |
| Methylisothiazolinone | 0.1-1.0 |
| Benzalkonium Chloride | 0.1-1.0 |
| Fragrance | 0.1-1.0 |

EXAMPLE 5

Another formulation is provided that can be used as a conditioner. The ingredients are included in the following approximate quantities.

| SUBSTANCE | WT/WT % Ranges |
|---|---|
| Salicylic Acid Non-Comedogenic Secondary Ingredients (other ingredients) | 0.5-2.0 |
| Water | 30.0-100 |
| Stearyl Alcohol | 0.1-30.0 |
| Cetyl Alcohol | 0.1-30.0 |
| *Prunus Amygdalus Dulcis* (Sweet Almond) Oil | 0.1-30.0 |
| Brassicamidopropyl Dimethylamine | 0.1-30.0 |
| Propylene Glycol | 0.1-10.0 |
| *Iris Florentina* Root Extract | 0.1-10.0 |
| Zinc Sulfate | 0.1-10.0 |
| Retinyl Palmitate | 0.1-1.0 |
| Copper PCA | 0.1-1.0 |

EXAMPLE 6

Another embodiment of the conditioner includes additional ingredients. This formulation is created by combining the following substances in the approximate ratios provided.

| SUBSTANCE | WT/WT % Ranges |
|---|---|
| Salicylic Acid | 0.5-2.0 |
| Non-Comedogenic Secondary Ingredients (other ingredients) | |
| Water | 30.0-100 |
| Stearyl Alcohol | 0.1-30.0 |
| Cetyl Alcohol | 0.1-30.0 |
| *Prunus Amygdalus Dulcis* (Sweet Almond) Oil | 0.1-30.0 |
| Brassicamidopropyl Dimethylamine | 0.1-30.0 |
| Propylene Glycol | 0.1-10.0 |
| *Iris Florentina* Root Extract | 0.1-10.0 |
| Zinc Sulfate | 0.1-10.0 |
| Alcohol | 0.1-10.0 |
| Retinyl Palmitate | 0.1-1.0 |
| Copper PCA | 0.1-1.0 |
| Panthenol | 0.1-1.0 |
| *Melaleuca Alternifolia* (Tea Tree) Leaf Oil | 0.1-1.0 |
| *Lavandula Angustifolia* (Lavender) Oil | 0.1-1.0 |
| *Sapindus Mukurossi* Fruit Extract | 0.1-1.0 |
| *Anthemis Nobilis* Flower Extract | 0.1-1.0 |
| Methylheptyl Isostearate | 0.1-1.0 |
| Tetrasodium EDTA | 0.1-1.0 |
| Methylchloroisothiazolinone | 0.1-1.0 |
| Methylisothiazolinone | 0.1-1.0 |
| Fragrance | 0.1-1.0 |

EXAMPLE 7

The conditioner as illustrated in Example 5 having the ingredient of Salicylic Acid used at 1.0% wt/wt.

| SUBSTANCE | WT/WT % Ranges |
|---|---|
| Salicylic Acid | 1.0 |
| Non-Comedogenic Secondary Ingredients (other ingredients) | |
| Water | 30.0-100 |
| Stearyl Alcohol | 0.1-30.0 |
| Cetyl Alcohol | 0.1-30.0 |
| *Prunus Amygdalus Dulcis* (Sweet Almond) Oil | 0.1-30.0 |
| Brassicamidopropyl Dimethylamine | 0.1-30.0 |
| Propylene Glycol | 0.1-10.0 |
| *Iris Florentina* Root Extract | 0.1-10.0 |
| Zinc Sulfate | 0.1-10.0 |
| Retinyl Palmitate | 0.1-1.0 |
| Copper PCA | 0.1-1.0 |

EXAMPLE 8

The conditioner as illustrated in Example 6 having the ingredient of Salicylic Acid used at 1.0% wt/wt.

| SUBSTANCE | WT/WT % Ranges |
|---|---|
| Salicylic Acid | 1.0 |
| Non-Comedogenic Secondary Ingredients (other ingredients) | |
| Water | 30.0-100 |
| Stearyl Alcohol | 0.1-30.0 |
| Cetyl Alcohol | 0.1-30.0 |
| *Prunus Amygdalus Dulcis* (Sweet Almond) Oil | 0.1-30.0 |
| Brassicamidopropyl Dimethylamine | 0.1-30.0 |
| Propylene Glycol | 0.1-10.0 |
| *Iris Florentina* Root Extract | 0.1-10.0 |
| Zinc Sulfate | 0.1-10.0 |
| Alcohol | 0.1-10.0 |
| Retinyl Palmitate | 0.1-1.0 |
| Copper PCA | 0.1-1.0 |
| Panthenol | 0.1-1.0 |
| *Melaleuca Alternifolia* (Tea Tree) Leaf Oil | 0.1-1.0 |
| *Lavandula Angustifolia* (Lavender) Oil | 0.1-1.0 |
| *Sapindus Mukurossi* Fruit Extract | 0.1-1.0 |
| *Anthemis Nobilis* Flower Extract | 0.1-1.0 |
| Methylheptyl Isostearate | 0.1-1.0 |
| Tetrasodium EDTA | 0.1-1.0 |
| Methylchloroisothiazolinone | 0.1-1.0 |
| Methylisothiazolinone | 0.1-1.0 |
| Fragrance | 0.1-1.0 |

EXAMPLE 9

Here, an embodiment of a formulation that can be used as a scalp treatment is provided. It is made by combining the following ingredients in the shown approximate percentages.

| SUBSTANCE | WT/WT % Ranges |
|---|---|
| Salicylic Acid | 0.5-2.0 |
| Non-Comedogenic Secondary Ingredients (other ingredients) | |
| Water | 30.0-100 |
| Polysorbate 80 | 0.1-30.0 |
| Butylene Glycol | 0.1-30.0 |
| Polysorbate 20 | 0.1-30.0 |
| Copper PCA | 0.1-10.0 |
| *Melaleuca Alternifolia* (Tea Tree) Leaf Oil | 0.1-10.0 |
| *Lavandula Angustifolia* (Lavender) Oil | 0.1-10.0 |
| *Prunus Amygdalus Dulcis* (Sweet Almond) Oil | 0.1-10.0 |
| *Anthemis Nobilis* Flower Extract | 0.1-10.0 |
| *Sapindus Mukurossi* Fruit Extract | 0.1-10.0 |
| Lactic Acid | 0.1-10.0 |
| DMDM Hydantoin | 0.1-1.0 |
| Potassium Sorbate | 0.1-1.0 |
| Xantham Gum | 0.1-1.0 |

EXAMPLE 10

Here, another embodiment of the scalp treatment is shown. It is created by combining the following ingredients in the approximate percentages provided.

| SUBSTANCE | WT/WT % Ranges |
|---|---|
| Salicylic Acid | 0.5-2.0 |
| Non-Comedogenic Secondary Ingredients (other ingredients) | |
| Water | 30.0-100 |
| Polysorbate 80 | 0.1-30.0 |
| Butylene Glycol | 0.1-30.0 |
| Polysorbate 20 | 0.1-30.0 |
| Copper PCA | 0.1-10.0 |
| *Melaleuca Alternifolia* (Tea Tree) Leaf Oil | 0.1-10.0 |
| *Lavandula Angustifolia* (Lavender) Oil | 0.1-10.0 |

-continued

| SUBSTANCE | WT/WT % Ranges |
|---|---|
| *Prunus Amygdalus Dulcis* (Sweet Almond) Oil | 0.1-10.0 |
| Lactic Acid | 0.1-10.0 |
| Fragrance | 0.1-10.0 |
| DMDM Hydantoin | 0.1-1.0 |
| Potassium Sorbate | 0.1-1.0 |
| Xantham Gum | 0.1-1.0 |
| *Anthemis Nobilis* Flower Extract | 0.1-10.0 |
| *Sapindus Mukurossi* Fruit Extract | 0.1-10.0 |
| Alcohol | 0.1-10.0 |
| Propylene Glycol | 0.1-10.0 |
| *Iris Florentina* Root Extract | 0.1-10.0 |
| Zinc Sulfate | 0.1-10.0 |
| Panthenol | 0.1-10.0 |
| Benzalkonium Chloride | 0.1-1.0 |

EXAMPLE 11

The scalp treatment as illustrated in Example 9 having the ingredient of Salicylic Acid used at 0.5% wt/wt.

| SUBSTANCE | WT/WT % Ranges |
|---|---|
| Salicylic Acid | 0.5 |
| Non-Comedogenic Secondary Ingredients (other ingredients) | |
| Water | 30.0-100 |
| Polysorbate 80 | 0.1-30.0 |
| Butylene Glycol | 0.1-30.0 |
| Polysorbate 20 | 0.1-30.0 |
| Copper PCA | 0.1-10.0 |
| *Melaleuca Alternifolia* (Tea Tree) Leaf Oil | 0.1-10.0 |
| *Lavandula Angustifolia* (Lavender) Oil | 0.1-10.0 |
| *Prunus Amygdalus Dulcis* (Sweet Almond) Oil | 0.1-10.0 |
| *Anthemis Nobilis* Flower Extract | 0.1-10.0 |
| *Sapindus Mukurossi* Fruit Extract | 0.1-10.0 |
| Lactic Acid | 0.1-10.0 |
| DMDM Hydantoin | 0.1-1.0 |
| Potassium Sorbate | 0.1-1.0 |
| Xantham Gum | 0.1-1.0 |

EXAMPLE 12

The scalp treatment as illustrated in Example 10 having the ingredient of Salicylic Acid used at 0.5% wt/wt.

| SUBSTANCE | WT/WT % Ranges |
|---|---|
| Salicylic Acid | 0.5 |
| Non-Comedogenic Secondary Ingredients (other ingredients) | |
| Water | 30.0-100 |
| Polysorbate 80 | 0.1-30.0 |
| Butylene Glycol | 0.1-30.0 |
| Polysorbate 20 | 0.1-30.0 |
| Copper PCA | 0.1-10.0 |
| *Melaleuca Alternifolia* (Tea Tree) Leaf Oil | 0.1-10.0 |
| *Lavandula Angustifolia* (Lavender) Oil | 0.1-10.0 |
| *Prunus Amygdalus Dulcis* (Sweet Almond) Oil | 0.1-10.0 |
| Lactic Acid | 0.1-10.0 |
| DMDM Hydantoin | 0.1-1.0 |
| Potassium Sorbate | 0.1-1.0 |
| Xantham Gum | 0.1-1.0 |

-continued

| SUBSTANCE | WT/WT % Ranges |
|---|---|
| *Anthemis Nobilis* Flower Extract | 0.1-10.0 |
| *Sapindus Mukurossi* Fruit Extract | 0.1-10.0 |
| Propylene Glycol | 0.1-10.0 |
| *Iris Florentina* Root Extract | 0.1-10.0 |
| Zinc Sulfate | 0.1-10.0 |
| Panthenol | 0.1-10.0 |
| Benzalkonium Chloride | 0.1-1.0 |

Other embodiments considered to be within the scope of the invention may include a variety of moisturizing, conditioning, and/or cleansing ingredients. These ingredients comprise: almond extract, chamomile extract, clover blossom extract, comfrey root extract, dandelion extract, dulse extract, fenugreek extract, hops extract, irish moss extract, kelp extract, melilot extract (hayflower), orange flower extract, peach extract, quince seed extract, rosemark extract, sage extract, sambucus (elder) extract, southern wood extract, fenugreek extract, henna extract, nettle extract, raspberry extract, rose bud extract, rosemary extract, sandal wood extract, thyme extract, violet extract, apple extract, avocado extract, burdock root extract, cactus extract, calendula extract (marigold), china bark extract (soap bark), clay sage extract, cleavers extract, Hawaiian white ginger extract, horsetail extract, kiwi extract, lemongrass extract, lemon peel extract, linden flower extract, madder root extract, oak moss extract, papaya extract, pineapple extract, primrose extract, quassia extract, soapwort extract, walnut extract (black), wild pansy extract, and yucca extract.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The above description is given by way of example, and not limitation. Given the above disclosure, one skilled in the art could devise variations that are within the scope and spirit of the invention disclosed herein, including various ways of treating and preventing conditions related to clogged pores, over or under production of sebum, inflammation, and/or excessive production of skin cells. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for treating acne, wherein the acne is face, neck, chest, shoulder, upper arm or back acne, comprising administering to hair and scalp of a subject in need of such treatment a topical non-comedogenic and non-sebum producing composition comprising salicylic acid in the range of about 0.5% to 2.0% w/w, sweet almond oil in the range of about 0.5% to 30% w/w, tea tree oil in the range of about 0.1% to 1.0% w/w, lavender oil in the range of about 0.1% to 1.0% w/w, *Iris Florentina* root extract in the range of about 0.1% to 10% w/w, *Sapindus Mukurossi* fruit extract in the range of about 0.1% to 1.0% w/w, *Anthemis Nobilis* flower extract in the range of about 0.1% to 1.0% w/w, and copper PCA in the range of about 0.1% to 1.0% w/w.

2. The method of claim 1, wherein salicylic acid is present in an amount of about 1.0% w/w.

3. The method of claim 2, wherein the composition further comprises retinyl palmitate is present in an amount of about 0.1% to 1.0% and zinc sulfate in an amount of about 0.1% to 10% w/w.

4. The method of claim 1, wherein the composition further comprises lactic acid.

5. The method of claim 4, wherein lactic acid is present in the range of about 0.1% to 10% w/w.

6. The method of claim 4, wherein the composition further comprises retinyl palmitate and benzalkonium chloride.

7. The method of claim 6, wherein retinyl palmitate is present in the range of about 0.1% to 1.0% w/w and benzalkonium chloride is present in the range of about 0.1 to 1.0% w/w.

* * * * *